US007633627B2

(12) United States Patent
Choma et al.

(10) Patent No.: US 7,633,627 B2
(45) Date of Patent: Dec. 15, 2009

(54) METHODS, SYSTEMS AND COMPUTER PROGRAM PRODUCTS FOR CHARACTERIZING STRUCTURES BASED ON INTERFEROMETRIC PHASE DATA

(75) Inventors: Michael Choma, Durham, NC (US); Joseph A. Izatt, Raleigh, NC (US); Audrey Ellerbee, Durham, NC (US); Marinko Sarunic, Durham, NC (US)

(73) Assignee: Duke University, Durham, NC (US)

( * ) Notice: Subject to any disclaimer, the term of this patent is extended or adjusted under 35 U.S.C. 154(b) by 236 days.

(21) Appl. No.: 11/337,166

(22) Filed: Jan. 20, 2006

(65) Prior Publication Data

US 2006/0256343 A1    Nov. 16, 2006

Related U.S. Application Data

(60) Provisional application No. 60/645,386, filed on Jan. 20, 2005.

(51) Int. Cl.
G01B 9/02    (2006.01)
(52) U.S. Cl. ..................................... 356/479
(58) Field of Classification Search ................. 356/450, 356/451, 452, 477, 479, 497
See application file for complete search history.

(56) References Cited

U.S. PATENT DOCUMENTS 5,153,669 A * 10/1992 DeGroot ..................... 356/489

5,398,113 A * 3/1995 de Groot ..................... 356/497
6,268,916 B1 * 7/2001 Lee et al. ..................... 356/369
2002/0085209 A1 * 7/2002 Mittleman et al. .......... 356/497
2004/0263859 A1    12/2004 Chang et al.

FOREIGN PATENT DOCUMENTS

WO    WO 98/38901    9/1998

OTHER PUBLICATIONS

Invitation to Pay Additional Fees and Partial International Search Report for application No. PCT/US2006/001936 mailed on May 29, 2006.
Arons et al. "Analysis of Fourier Synthesis Holography for Imaging Through Scattering Materials" *Applied Optics* 34 (11): 1841-1847 (1995).

(Continued)

*Primary Examiner*—Gregory J Toatley, Jr.
*Assistant Examiner*—Scott M Richey
(74) *Attorney, Agent, or Firm*—Myers Bigel Sibley & Sajovec

(57) ABSTRACT

Structure profiles from optical interferometric data can be identified by obtaining a plurality of broadband interferometric optical profiles of a structure as a function of structure depth in an axial direction. Each of the plurality of interferometric optical profiles include a reference signal propagated through a reference path and a sample signal reflected from a sample reflector in the axial direction. An axial position corresponding to at least a portion of the structure is selected. Phase variations of the plurality of interferometric optical profiles are determined at the selected axial position. A physical displacement of the structure is identified based on the phase variations at the selected axial position.

27 Claims, 8 Drawing Sheets

OTHER PUBLICATIONS

Blazkiewicz et al. "Signal-to-Noise Ratio Study of Full-Field Fourier-Domain Optical Coherence Tomography" *Applied Optics* 44(36): 7722-7729 (2005).

Youngquist et al. "Optical Coherence Domain Reflectometry: A New Optical Evaluation Technique" *Opt Lett* 12(3):158-160 (1987).

Takada et al. "New Measurement System for Fault Location in Optical Waveguide Devices Based on an Interferometric Technique" *Applied Optics* 26(9): 1603-1606 (1987).

Danielson et al. "Guided-Wave Reflectometry with Micrometer Resolution" *Applied Optics* 26(14): 2836-2842 (1987).

* cited by examiner

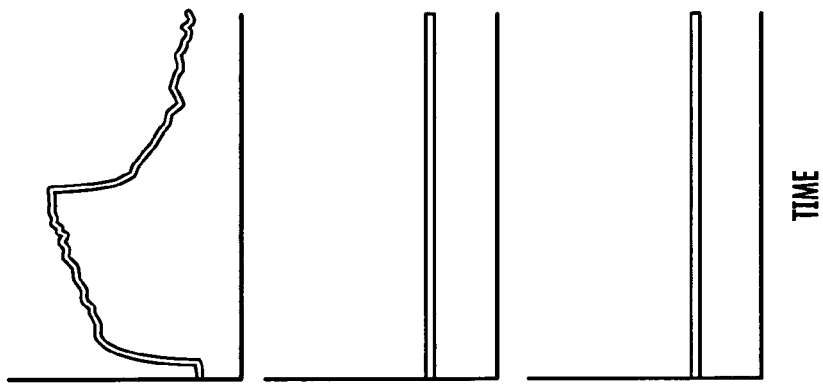
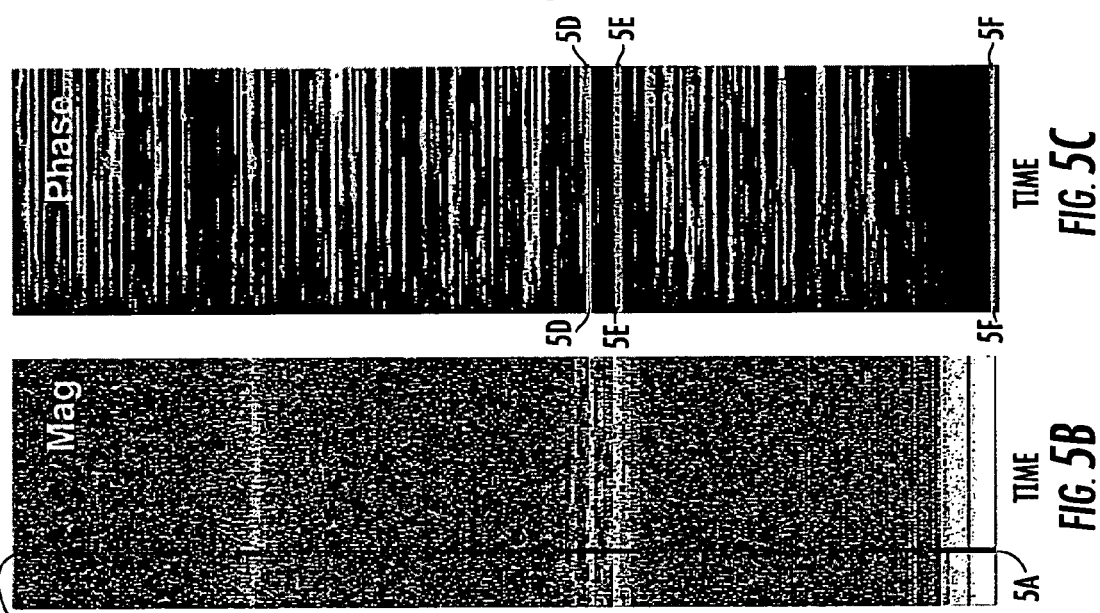
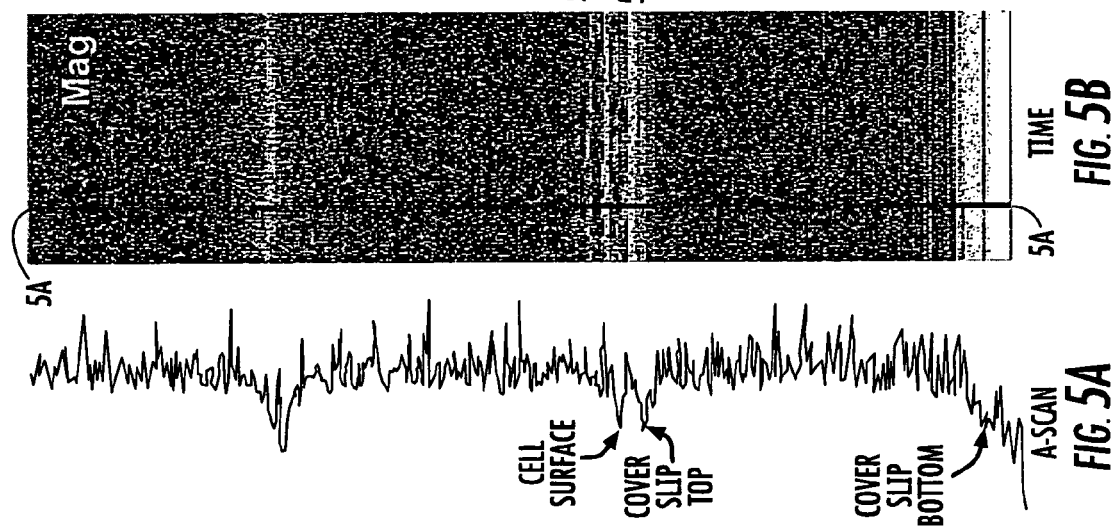

METHODS, SYSTEMS AND COMPUTER PROGRAM PRODUCTS FOR CHARACTERIZING STRUCTURES BASED ON INTERFEROMETRIC PHASE DATA

RELATED APPLICATIONS

This application claims priority to U.S. Provisional Application Ser. No. 60/645,386 filed Jan. 20, 2005, the disclosure of which is hereby incorporated by reference in its entirety.

STATEMENT OF GOVERNMENT SUPPORT

This invention was made with Government support under grant number 5R24-EB00243 from the National Institutes of Health. The Government has certain rights to this invention.

BACKGROUND OF THE INVENTION

The present invention relates to methods and systems for imaging, and more particularly, to interferometric structure imaging and characterization.

Since its introduction in the early 1990's, optical coherence tomography (OCT) has emerged as a promising imaging modality for micrometer-scale noninvasive imaging in biological and biomedical applications. Its relatively low cost and real-time, in vivo capabilities have fueled the investigation of this technique for applications in retinal and anterior segment imaging in ophthalmology (e.g., to detect retinal pathologies), early cancer detection and staging in the skin, gastrointestinal, and genitourinary tracts, as well as for ultra-high resolution imaging of entire animals in embryology and developmental biology. Conventional OCT systems are essentially range-gated low-coherence interferometers that have been configured for characterization of the scattering properties of biological and other samples. By measuring singly backscattered light as a function of depth, OCT fills a valuable niche in imaging of tissue ultrastructure, and provides subsurface imaging with high spatial resolution (~1-10 µm) in three dimensions and high sensitivity (>110 dB) in vivo with no contact needed between the probe and the tissue. OCT is based on the one-dimensional technique of optical coherence domain reflectometry (OCDR), also called optical low-coherence reflectometry (OLCR). See Youngquist, R. C., S. Carr, and D. E. N. Davies, *Optical Coherence Domain Reflectometry: A New Optical Evaluation Technique*. Opt. Lett., 1987. 12: p. 158; Takada, K., et al., *New measurement system for fault location in optical waveguide devices based on an interferometric technique*. Applied Optics, 1987. 26(9): p. 1603-1606; and Danielson, B. L. and C. D. Whittenberg, *Guided-wave Reflectometry with Micrometer Resolution*. Applied Optics, 1987. 26(14): p. 2836-2842. In some instances of time-domain OCT, depth in the sample is gated by low coherence interferometry. The sample is placed in the sample arm of a Michelson interferometer, and a scanning optical delay line is located in the reference arm.

The time-domain approach used in conventional OCT has been used in supporting biological and medical applications. An alternate approach involves acquiring as a function of optical wavenumber the interferometric signal generated by mixing sample light with reference light at a fixed group delay. Two methods have been developed which employ this Fourier domain (FD) approach. The first is generally referred to as Spectral-domain OCT (SD-OCT). SD-OCT uses a broadband light source and achieves spectral discrimination with a dispersive spectrometer in the detector arm. The second is generally referred to as swept-source OCT (SS-OCT). SS-OCT time-encodes wavenumber by rapidly tuning a narrowband source through a broad optical bandwidth. Both of these techniques can provide improvements in SNR of up to 15-20 dB when compared to time-domain OCT, because SD-OCT and SS-OCT capture the complex reflectivity profile (the magnitude of which is generally referred to as the "A-scan" data or depth-resolved sample reflectivity profile) in parallel. This is in contrast to time-domain OCT, where destructive interference is employed to isolate the interferometric signal from only one depth at a time as the reference delay is scanned.

However, the resolution of current OCT techniques is generally limited by the coherence length of the illumination source. Therefore, current OCT techniques may not be able to resolve structures of less than ~1-10 µm. For example, the characteristics and dynamics of the cellular surface may be of interest in many areas of quantitative biology. However, there are few scientific tools which are capable of noninvasively acquiring quantitative information about cell surface profiles, displacements, and motions on the nanometer scale.

Dramatic improvements in spatial resolution in optical microscopy have resulted from the development of confocal, multiphoton, standing wave interferometric, fluorescence depletion, and point-spread function-engineered apodization techniques, among others. However, some of these techniques which operate noninvasively in the optical far field have so far been limited to spatial resolutions of about $\lambda/10$ or on the order of 50 nm. Substantially better resolution is routinely acquired with scanning probe microscopies, including atomic force microscopy (AFM), scanning tunneling microscopy (STM), and scanning near-field optical microscopy (SNOM). These techniques are the diagnostic workhorses of modern nanoscience and nanotechnology, however their innate contact or near-contact operation is by definition invasive to the surface structure under examination. This invasiveness can take the form of mechanical disruption of the surface structures of interest, or alternatively interfering with or blocking the interaction of surface structures with their environment.

SUMMARY OF EMBODIMENTS OF THE INVENTION

According to embodiments of the present invention, structure profiles from optical interferometric data can be identified by obtaining a plurality of broadband interferometric optical profiles of a structure as a function of structure depth in an axial direction. Each of the plurality of interferometric optical profiles include a reference signal propagated through a reference path and a sample signal reflected from a sample reflector in the axial direction. An axial position corresponding to at least a portion of the structure is selected. Phase variations of the plurality of interferometric optical profiles are determined at the selected axial position. A physical displacement of the structure is identified based on the phase variations at the selected axial position.

According to some embodiments of the present invention, a system for identifying structure profiles from optical interferometric data includes an interferometer configured to acquire a plurality of broadband interferometric profiles of a structure as a function of structure depth in an axial direction. Each of the plurality of interferometric optical profiles include a reference signal propagated through a reference path and a sample signal reflected from a sample reflector in the axial direction. A signal analyzer is configured to select an axial position corresponding to at least a portion of the structure, to determine phase variations of the plurality of interferometric optical profiles at the selected axial position, and to identify a physical displacement of the structure based on the phase variations at the selected axial position.

While the invention has been described above primarily with respect to the various method and system aspects of the invention, computer program products are also provided.

BRIEF DESCRIPTION OF THE DRAWINGS

FIGS. 5A-5F are graphs illustrating temporal profiling of a sample having a cell on a glass cover slip according to embodiments of the present invention. FIG. 5A is an A-Scan (or magnitude of the complex reflectivity profile of the sample). FIG. 5B is the magnitude of the positive frequencies of the complex reflectivity profile plotted in gray-scale as a function of time. FIG. 5C is the phase of the positive frequencies of the complex reflectivity profile as a function of time. FIG. 5D is the phase difference between the scans at a pixel depth corresponding to the surface of the cell. FIGS. 5E and 5F are the phase differences between the scans at a pixel depth corresponding to the top and bottom of the cover slip, respectively.

FIG. 7A is a graph of a three-dimensional data cube of a reflected interference signal in two lateral dimensions. FIG. 7B is a graph of a selected spectrum from the data of FIG. 7A. FIG. 7C is a graph of the spectrum of FIG. 7B re-sampled in wavenumber. FIG. 7D is a graph of re-sampled data that has been Fourier transformed to generate a complex reflectivity profile having an amplitude and phase. FIG. 7E is a graph of a three-dimensional data cube that illustrates the interferometric phase of each spectrum as shown in FIG. 7D converted to axial distance. FIG. 7F is a graph of two-dimensional nanoscale resolution axial distance profile extracted from the data block of FIG. 7E.

DETAILED DESCRIPTION OF EMBODIMENTS OF THE INVENTION

Figure 1:
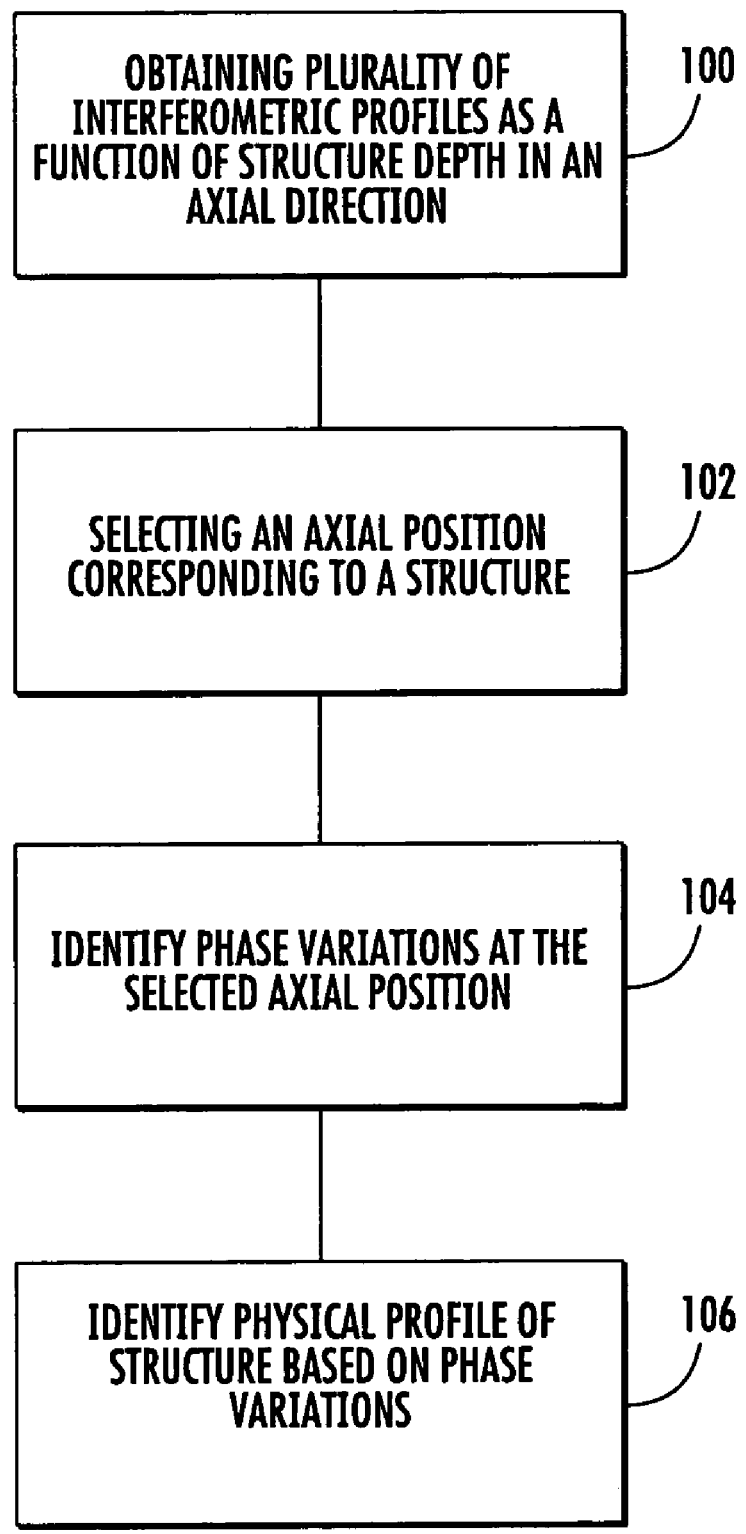
FIG. 1 is a flowchart illustrating operations according to embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. It will also be appreciated by those of skill in the art that references to a structure or feature that is disposed "adjacent" another feature may have portions that overlap or underlie the adjacent feature.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer (such as interferometer device), and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM) or digital video disk (DVD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the invention may be carried out on human subjects for diagnostic or prognostic purposes, and may be carried out on animal subjects such as dogs, cats, or mice for veterinary or research purposes. Embodiments of the invention may be carried out in vivo or ex vivo, for example, on cells or other living or nonliving tissue.

As used herein, "light" refers to optical radiation suitable in the ultraviolet, visible or infrared spectra, and includes optical radiation suitable for low coherence interferometry.

As used herein, "broadband" refers to a spectral bandwidth that is greater than about 10 nanometers. "Low coherence" refers to a coherence length of less than about 100 microns. Low coherence or broadband interferometric data refers to data obtained with a low coherence or broadband light source, or interferometric data synthesized by sweeping a narrowband or coherent light source through a broad spectral range.

According to embodiments of the present invention, structure profiles can be identified from optical interferometric data. As shown in FIG. 1, a plurality of interferometric optical profiles of a structure as a function of structure depth in an axial direction can be obtained (Block 100). The axial direction is generally the direction of propagation of the incident optical beam. The interferometric optical profiles include an interference signal of a reference signal reflected from a reference reflector and a sample signal reflected from a sample reflector. In some embodiments, the interferometric optical profile is a Fourier transformed complex reflectivity profile obtained from a broadband spectral interferogram. An axial position corresponding to at least a portion of the structure can be selected (Block 102). The axial position can be selected based on a conventional Optical Coherence Tomography (OCT) scan that can be used to identify the location of a structure of interest. Phase variations of the plurality of interferometric optical profiles at the selected axial position can be determined (Block 104). A physical profile, such as the displacement of the structure, can be identified based on the phase variations at the selected axial position (Block 106). The plurality of interferometric optical profiles and/or the phase variations between the optical profiles is referred to herein as "Spectral Domain Phase Microscopy (SDPM)" data.

The resolution of conventional optical coherence tomography (OCT) is generally limited by the coherence length of the illumination source. However, according to embodiments of the present invention, the analysis of phase variations between a plurality of optical interferometric profiles at a selected position can provide sub-coherence length resolution. For example, the physical displacement of the structure can be determined with a resolution of less than about 100 nanometers. In some embodiments, the resolution can be determined to within 10 nanometers or one nanometer or less.

In some embodiments, the interferometric optical profiles can be obtained within a selected axial position range or region at a given lateral position over time, and the axial physical displacement (e.g., movement) of the structure can be determined. In other embodiments, the interferometric optical profiles can be obtained within the selected axial position region as a function of lateral position, and the lateral physical displacement (e.g., lateral structure variations) can be determined. Accordingly, sub-nanometer scale motions and/or profiles may be obtained. Sub-wavelength phase information can be position-gated from low coherence data. White light interferometry (WLI) full-field or scanning techniques can be used to measure structure including the topography or variations within a sample interior.

Figure 2:
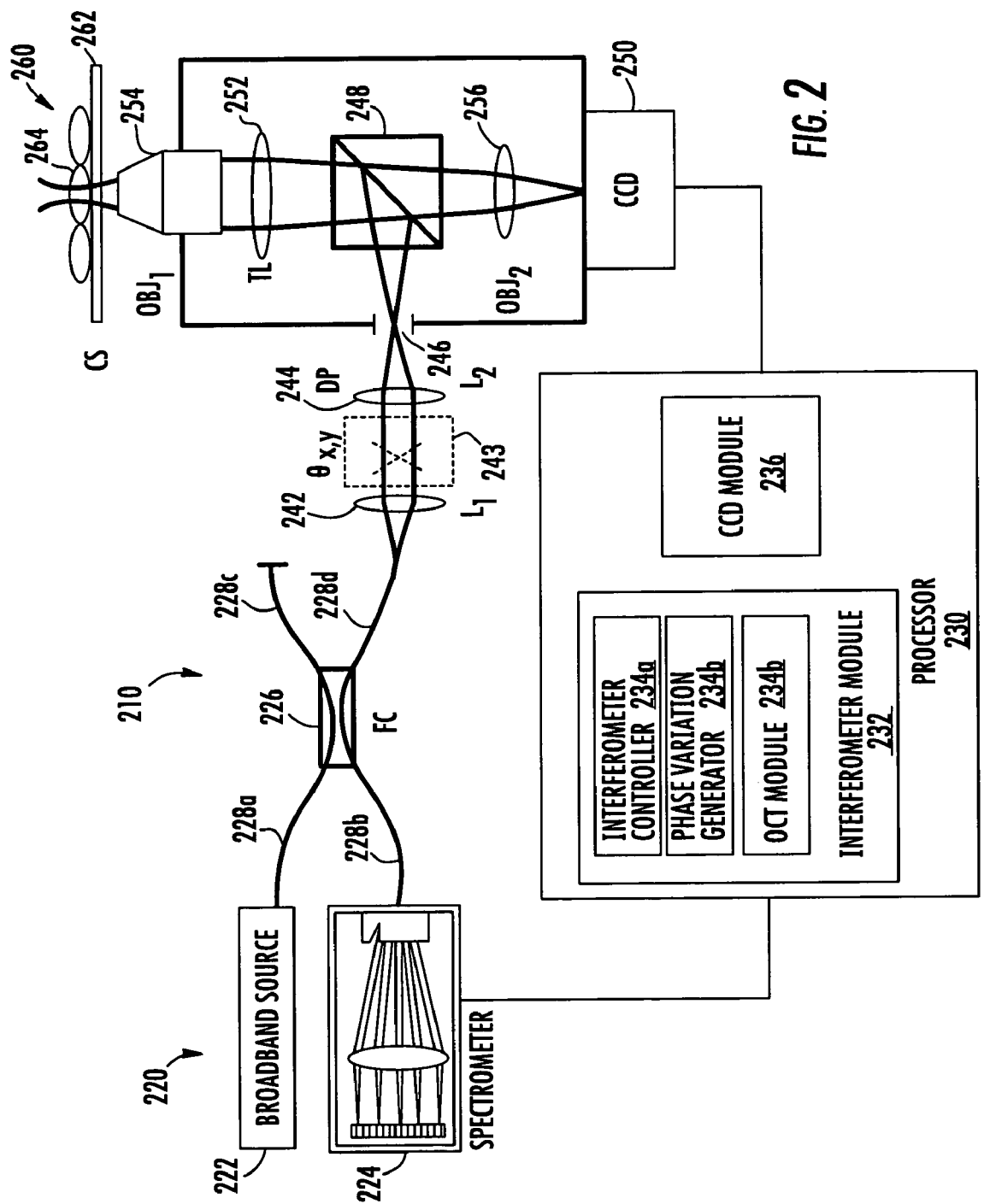
FIG. 2 is a schematic diagram of optical systems and methods according to embodiments of the present invention including a broadband source and a spectrometer.

The plurality of interferometric optical profiles can be acquired using an interferometric system, such as the optical system 210 illustrated in FIG. 2. The optical system 210 includes an interferometer assembly 220 and a processor 230. The interferometer assembly 220 includes a sample optical assembly 240. The interferometer assembly 220 also includes a broadband light source 222 and a spectrometer 224 connected to a fiber coupler 226 by a source optical fiber 228a and a spectrometer fiber 228b. The fiber coupler 226 has two output optical fibers 228c and 228d. The sample optical assembly 240 includes a collimating lens 242, a galvanometer-driven mirror pair for lateral beam scanning $\theta_{x,y}$ 243, an objective lens 244, a documentation port 246, a beam splitter 248, a CCD camera 250, a tube lens 252, a microscope objective lens 254, a camera objective lens 256, and a sample 260. The processor 230 includes an interferometer module 232 and a CCD module 236. The processor 230 is configured to receive and analyze data from the interferometer assembly 220 and the CCD camera 250.

As illustrated, the sample 260 is a biological cell 264 on a glass slide or cover slip 262. In particular embodiments, the physical displacement of the cell structures, such as the surface of the cell 264 can be determined. However, other samples may be provided, including living and non-living samples.

As shown in FIG. 2, light from the broadband source 222 passes through the optical fiber 228a to the optical fiber 228d via the fiber coupler 226. Light from the optical fiber 228d is collimated by the collimating lens 242 and passes through the object lens 244 to the documentation port 246 of the sample optical assembly 240. Light travels to the sample 260 via the beam splitter 248, the tube lens 252 and the microscope objective lens 254. Light that is reflected from the sample 260 is split by the beam splitter 248 and travels to the CCD camera 250 (via the objective lens 256) and the interferometer assembly 220 (via the lenses 242 and 244, the optical fiber 228d, the fiber coupler 226 and the optical fiber 228b).

In this configuration, the spectrometer 224 and the CCD camera 250 receive a broadband light signal that is reflected from the sample 260. The CCD camera 250 uses the light signal to provide an image of the sample 260, for example, using conventional CCD imaging techniques. The spectrometer 224 measures various wavelengths from the sample 260 to provide spectral interferometric signals.

As illustrated, the interferometric signal provided by the spectrometer 224 is the interference pattern between a reference signal that is reflected from the cover slip 262 and a sample signal that is reflected from the cell(s) 264 in an axial direction. The cover 262 slip may be used as a reference reflection because it is a relatively strong reflection (typically 4% due to the Fresnel reflection from the air-glass index interface), and it is sufficiently separated from the surface of the cells 264 to avoid phase corruption as discussed below. Phase corruption may occur when multiple reflectors are spaced closer together than a coherence length. In some embodiments, the surface of the cover slip 262 that is opposite the cell 264 is used as a reference reflector, and the surface of the cover slip 262 that is adjacent the cell 264 is coated with an anti-reflection coating to avoid multiple reference reflections. Configurations in which the reference signal and the sample signal generally share a common pathway may be referred to as a "common path" configuration. A common path configuration may increase the phase stability of the signals, which can increase structural resolution. In some embodiments, the common path configuration can result in a phase stability that is increased by at least a factor of two or more. In particular embodiments, the phase stability may be increased by a factor of ten or more over non-common path techniques. However, it should be understood that other configurations can be used. For example, the optical fiber 228c may be optically connected to a reference reflector to provide the reference signal.

The processor 230 receives data from the interferometer assembly 220 and the CCD camera 250. The data can be analyzed by the interferometer module 232 and the CCD module 236, respectively. The interferometer module 232 includes an interferometer controller 234a, a phase variation generator 234b and an OCT module 234c. The interferometer controller 234a controls the interferometer assembly 220 to obtain the desired interferometric data from the optical system 210. For example, the controller 234a can obtain a plurality of interferometric optical profiles of the sample 260 as a function of structure depth in the axial direction. The interferometric optical profiles can be a Fourier transform complex reflectivity profile of a broadband spectral interferogram. The phase variation generator 234b can determine phase variations of the interferometric optical profiles at a selected axial position and identify a physical displacement of the structure based on the phase variations at the selected axial position. In addition, the OCT module 234c can provide OCT imaging based on the interferometric optical profiles of the sample 260.

In some embodiments, an OCT image of the sample 260 from the OCT module 234c can be used to select an axial position in the sample 260, and the phase variation generator 234b can generate phase variations at the selected axial position. For example, a user can select an axial position corresponding to a structure in the sample 260. In other embodiments, a plurality of axial positions or all axial positions of a dataset can be selected and imaged according to the techniques described herein. In some embodiments, the CCD module 236 generates an image of the sample 260, and the user can select the lateral position based on the CCD image.

Figure 3:
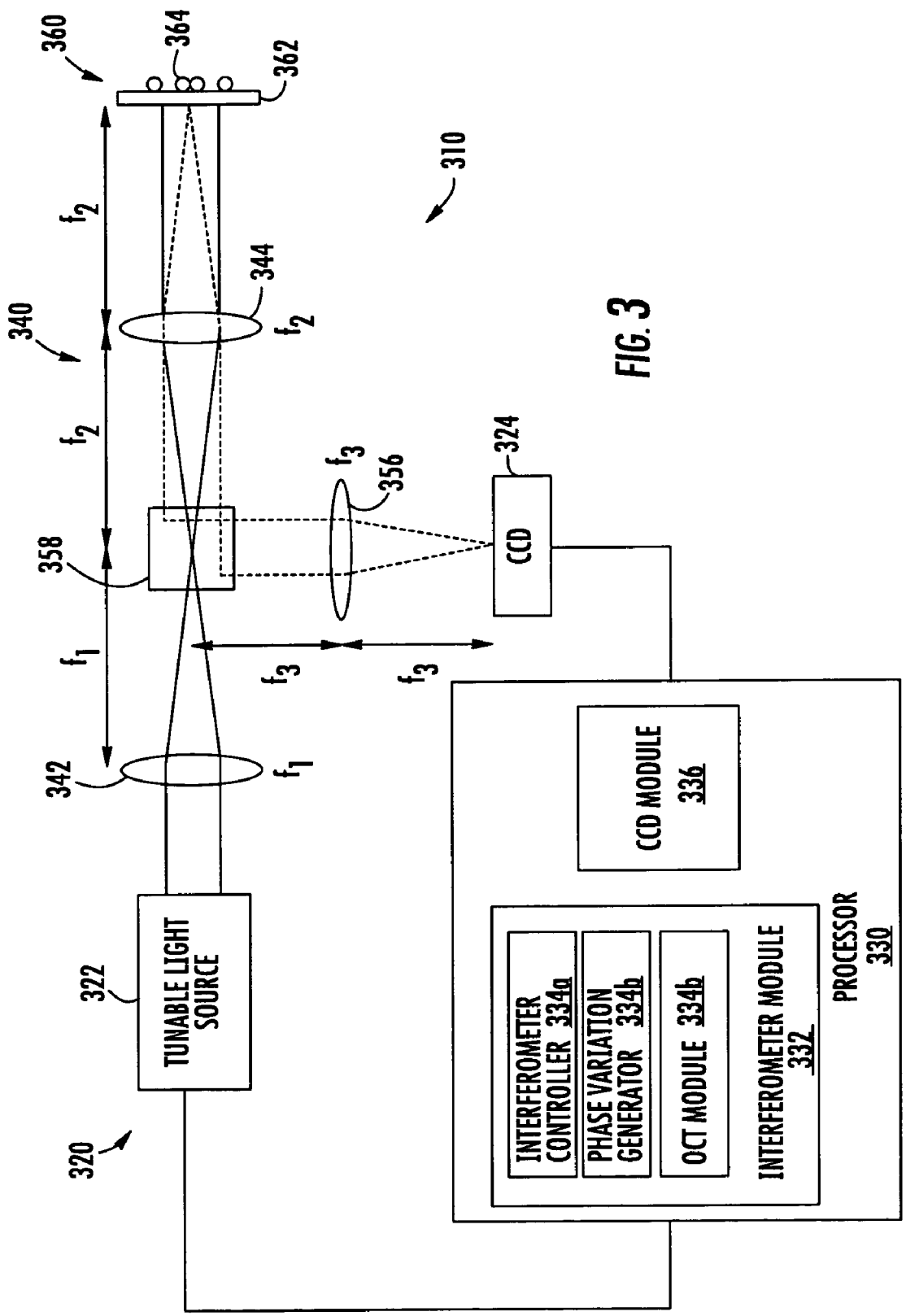
FIG. 3 is a schematic diagram of optical systems according to further embodiments of the present invention including a swept source and a photodetector array.

As illustrated, the optical system 210 of FIG. 2 includes a broadband source 222 (i.e., to provide a spectral domain interferometer); however, other light sources can be used. For example, a swept source interferometer configuration is illustrated in FIG. 3. An optical system 310 in FIG. 3 includes an interferometer assembly 320 and a processor 330. The interferometer assembly 320 includes an optical assembly 340 and a tunable wavelength source 322. The optical assembly includes lenses 342, 344, and 356, a beamsplitter 358, a CCD camera 324 and a sample 360. The sample 360 includes a cover slip 362 and cells 364. As illustrated, the tunable wavelength source 322 is a narrrowband source that is rapidly tuned through a broad optical bandwidth to provide an interferometric signal. It should be understood that any suitable tunable light sources may be used, such as a tunable laser source or a broadband light source with a tunable filter placed between it and the bulk-optic interferometer 324. The CCD camera 324 can be a one- or two-dimensional CCD array, and can be used to provide microscopic imaging and/or detection of an interferometric signal. The processor 330 and the components thereof corresponds generally to the processor 230 of FIG. 2.

Although optical systems according to the present invention are described with respect to the optical systems 210 and 310, it should be understood that other configurations can be used, including optical configurations suitable for obtaining OCT data. For example, the fiber coupler 226 and optical fiber 228d can be omitted, and an optical circulator can be used to connect the fibers 228a, 228b and 228d, which may provide efficient collection of mixed light returning from the sample 260. In particular, an optical circulator can be configured such that light from the broadband source 222 travels through fiber 228a to fiber 228d and the sample system 240, and light from the sample system 240 passes through fiber 228d and to fiber 228b and the spectrometer 224.

Figure 4B:
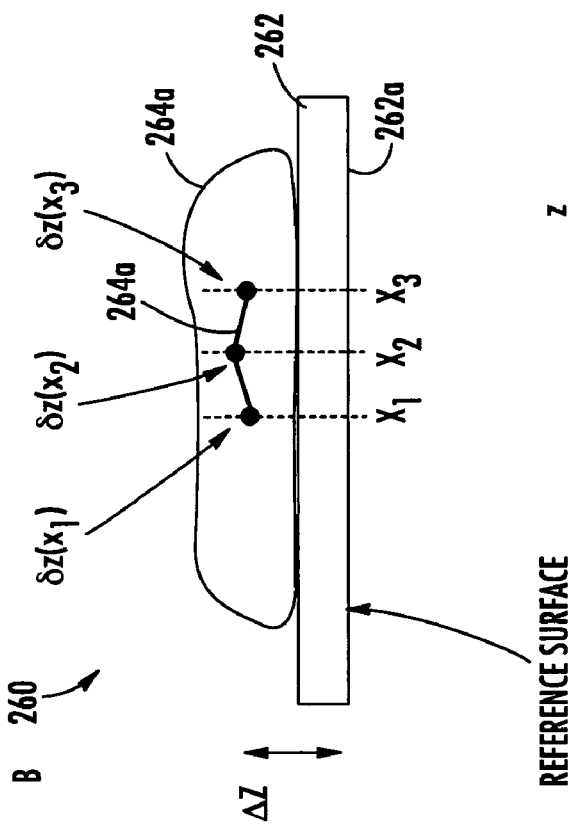
FIGS. 4A-4B are schematic diagrams illustrating temporal profile of a sample structure (FIG. 4A) and spatial profiling of a sample structure (FIG. 4B) according to embodiments of the present invention.
Figure 4A:
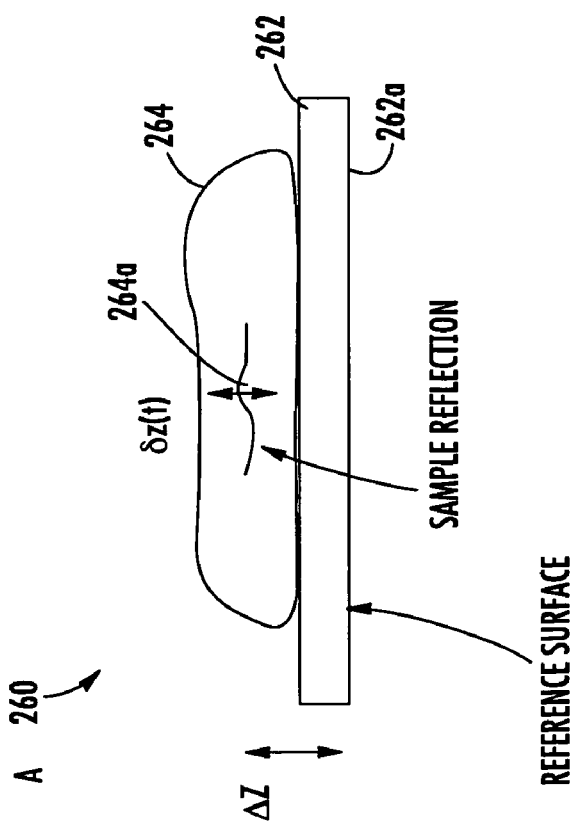

As shown in FIGS. 4A-4B, the cover slip 262 includes a reference surface 262a for providing a reference reflection, and the cell 264 includes a structure or sample reflector 264a. A displacement profile of the sample 260 can be obtained as a function of time ($\delta z(t)$ in FIG. 4A) or as a function of space ($\delta z(x)$ in FIG. 4B). In FIGS. 4A-4B, $\Delta z$ is the optical path length difference between the reference surface 262a and the sample reflector 264a, and may be sufficiently large so as to be detected using conventional OCT. Without wishing to be bound by theory, the resolution of a structure using conventional OCT is generally limited by the coherence length of the light used to obtain an interferogram. The axial position of the sample reflector 264a as a function of time $\delta z(t)$ (FIG. 4A) or as a function of lateral position $\delta z(x)$ (FIG. 4B) may be small compared to the coherence length such that $\delta z(t)$ and $\delta z(x)$ may not be effectively resolved using conventional OCT. According to embodiments of the present invention, profiles of the positions of sample reflectors (such as reflector 264a) can be construed from repeated measurements of the optical phase corresponding to the position of the sample reflector 264a. These measurements may be phase unwrapped as desired.

As shown in FIG. 4A, repeated phase measurements may be made at a given lateral (x,y) and axial ($\Delta z$) position to provide a displacement profile as a function of time $\delta z(t)$ of the sample reflector 264a. As shown in FIG. 4B, repeated phase measurements may be made at a given axial position ($\Delta z$) to provide a spatial displacement profile as a function of lateral spatial dimensions $\delta z(x)$ by raster scanning either the sample beam or the sample 264 in one or both lateral dimensions x or y to obtain one- or two-dimensional spatial profiles of the reflector 264a, respectively.

In some embodiments, focusing optics can be designed and selected to deliver a desired spot size defining the lateral resolution on the sample 264 at the sample reflector 264a and to deliver a suitable reference reflection from the reference reflector 262a. Considerations for optimizing the amplitude of the reference reflection, given the intensity and noise properties of the light source, may be similar to those used in other implementations of Fourier-domain OCT.

Although embodiments according to the present invention are described herein with respect to detecting physical displacements of a structure over time or as a lateral structure profile, it should be understood that phase variations between interferometric optical profiles may be used to determine other physical characteristics. For example, phase variations between interferometric optical profiles can be used to measure the index of refraction of a medium or the index of refraction ratio at a boundary between two media.

Embodiments according to the present invention will now be described with respect to the following non-limiting examples.

Exemplary Calculations

The spectral interferogram signal recorded in all FDOCT systems generally contains both amplitude and phase information about the sample optical field relative to the reference field. For example, the spectral interferogram data contains direct current (DC) components (corresponding to non-interfering light returning from the sample and reference paths), auto-correlation components (corresponding to interference between different reflectors in the same sample), and cross-correlation components (corresponding to the desired interference between reference and sample paths). Also, SDOCT techniques tend to collect spectral interferogram data evenly sampled in wavelength rather than wavenumber, since grating-based spectrometers disperse light according to wavelength. Various techniques for designing systems to avoid substantial autocorrelation signals and for re-sampling FDOCT data so that it is evenly sampled in wavenumber (k) are known and will not be further described.

For an SDOCT system, the DC and cross-correlation components of the re-sampled photocurrent i(k) at the spectrometer due to a single sample reflector are described by Eq. (1) (a similar equation describes the photocurrent signal from an SSOCT system):

$$i(k) \propto \rho S(k) \delta k \Delta t [R_R + R_S + 2\sqrt{R_R R_S} \cos(2nk[\Delta z + \delta z])]. \quad (1)$$

Here, $\Delta z + \delta z$ gives the position of the sample reflector defined by the path length difference between it and the reference reflector, n is the average group index of refraction of the material over the path length difference $\Delta z + \delta z$, $\rho$ is the detector responsivity, $S(k)$ is the source power density function, $\delta k$ is the spectrometer spectral resolution, $\Delta t$ is the spectrometer integration time, and $R_R$ and $R_S$ are the reference and sample reflectivities, respectively. $\Delta z$ indicates the reflector position to within the axial resolution of the system (determined by the coherence length of the light source used), whereas $\delta z$ represents sub-resolution departures of position from $\Delta z$. The symbol k represents wavenumber, which is inversely proportional to wavelength according to $k = 2\pi/\lambda$.

Procedures for signal processing in FDOCT can involve an inverse Fourier transform of i(k) to give I(z), a one dimensional, depth-resolved, complex-valued reflectivity profile. A signal of interest in FDOCT is the magnitude of the complex reflectivity profile |I(z)|, which is typically referred to as the "A-scan," or depth-resolved sample reflectivity profile. This profile has peak values at $x = \pm 2n\Delta z$, corresponding to the reflector position. The magnitude and phase of I(z) evaluated at these peaks are:

$$|I(\pm 2n\Delta z)| = (\rho/2e) S(k) \Delta t \sqrt{R_R R_S} E(2n\Delta z), \quad (2)$$

$$\angle I(\pm 2n\Delta z) = \pm j2nk_0 \delta z \quad (3)$$

where $E(2n\Delta z)$ is the unity-amplitude time-domain coherence envelope function, $k_0$ is the source center wavenumber, and $\angle$ is the phase operator. The presence of mirror-image peaks at both positive and negative displacements is referred to as the complex conjugate ambiguity artifact in FDOCT.

In order to sub-resolve structure profiles as a function of time and/or lateral dimension, the interferometric phase is obtained at the depth in the sample corresponding to the structure of interest, i.e. at $I(\pm 2n\Delta z)$. Phase and displacement are linearly related at the reflectivity peaks, and conversion from one to the other is accomplished using:

$$\delta z(t) = \frac{1}{2nk_0} (\angle I(2n\Delta z, t) - \angle I(2n\Delta z, t_o)), \quad (4)$$

in the case of temporal profiling (where t and $t_0$ are temporally sequential spectral interferogram acquisition times), or $$\delta z(t) = \frac{1}{2nk_0} (\angle I(2n\Delta z, x) - \angle I(2n\Delta z, x_o)), \quad (5)$$

in the case of spatial profiling (where x and $x_0$ are laterally separated spectral interferogram acquisition positions). Using these equations, physical displacements of sub-resolution changes in reflector position can be tracked as a function of time or lateral dimension over several coherence lengths (i.e. the region over which the coherence envelope is above the noise floor). In some embodiments, $\delta z$ varies slowly enough with respect to $(t-t_0)$ or $(x-x_0)$ to allow for phase unwrapping.

Illustration of this procedure in the case of temporal profiling is illustrated in FIGS. 5A-5F. FIGS. 5B-5F illustrate a sequence of spectral interferogram acquisitions at a fixed lateral position on a cell surface. The sample is a cell on a glass cover slip. A magnetic bead is positioned on the cell, and a magnet tip is positioned over the bead to cause movement of the bead and the cell surface (not shown). FIG. 5A is an A-Scan (or magnitude of the complex reflectivity profile of the sample) at the time indicated by the vertical line 5A in FIG. 5B. FIG. 5B is the magnitude of the positive frequencies of the complex reflectivity profile plotted in gray-scale as a function of time. FIG. 5C is the phase of the positive frequencies of the complex reflectivity profile plotted in gray-scale as a function of time. FIG. 5D is the phase difference between the scans at a pixel depth corresponding to the surface of the cell (illustrated by the position of the horizontal line 5D in FIG. 5C). FIGS. 5E and 5F are the phase differences between the scans at a pixel depth corresponding to the top and bottom of the cover slip, respectively (illustrated by the position of the horizontal lines 5E and 5F, respectively in FIG. 5C).

From the magnitude or A-scan data of FIG. 5A, it is possible to identify the reflections corresponding to the bottom surface of the cover slip, the top surface of the cover slip, and the cell surface. The identified pixel depth of these structures are used to extract the phase data at the same depth pixel, and results in plots of the temporal displacement of the bottom surface of the cover slip (FIG. 5F), the top surface of the cover slip (FIG. 5E) and the cell surface (FIG. 5D) over the acquisition time of the spectral interferograms. In this case, the bottom and top surfaces of the cover slip remain essentially fixed as shown in FIGS. 5D-5F, while the cell surface moved in response to the movement of the magnetic bead as shown in FIG. 5D.

The resolution of such displacement measurements may be limited by the phase stability of I(z). Phase stability can be increased through the use of a common path setup as described with respect to FIGS. 2-3, in which much of the phase noise is common-mode. In some embodiments, the resolution of the displacement measurements can be reduced by using a broadband source and spectrometer (i.e., SDOCT), in which case there are no moving parts. In contrast, an SSOCT setup can include a tunable source, which typically includes moving parts. In the limit of stable separate reference and sample arms, the sensitivity of displacement measurements described herein may be a function of the SNR of the sampled reflector. A fundamental lower limit on the displacement sensitivity of δz(t) due to shot noise may be derived by generalizing i(k) to contain an additive, uncorrelated Gaussian white noise term. For example, the sensitivity of δz(t) may be an explicit function of the signal-to-noise ratio (SNR) of the signal from the reflector whose displacement is being measured as follows:

$$\delta z_{sens} \approx \frac{\lambda_o}{4n\pi} \sqrt{\frac{1}{SNR(S, \Delta t, R_s)}} \quad (6)$$

Temporal Profiling of a Glass Cover Slip

One-dimensional temporal profiling using the systems described in FIGS. 2-3 (i.e., both SDOCT and SSOCT interferometers) have been performed. The theoretical sensitivity as been derived and verified in measuring displacements of a sample reflector. It is noted that both SDOCT and SSOCT approaches were considered because 1) both are suitable for differential temporal and spatial profiling and 2) each technique has its particular advantages (e.g., FDOCT may exhibits exceptional phase stability due to the absence of moving parts, but typically requires resampling from wavelength to wavenumber space, while an SSOCT signal can be linearly sampled in wavenumber space). Initial measurements of the displacement stability using the top of the cover slip as the sample reflection, recorded as the standard deviation of repeated displacement measurements, yielded displacement stability of 53 pm for the Fourier-domain implementation and 780 pm for the swept-source implementation.

Temporal Profiling in Living Cells

One-dimensional temporal profiling of displacements in living biological cells has been performed using the phase variations between a plurality of interferometric optical profiles as described herein. The optical system 210 in FIG. 2 was aligned to position the interferometer focus of the interferometer assembly 220 coplanar with the microscope's object plane focus of the CCD camera 250; an aiming beam (635 nm) coupled into the source fiber (not shown in FIG. 2) permitted visualization of the location from which data were collected. The beam was turned off during the experiment, but was replaced with a visual marker using video overlay. The charge-coupled device (CCD) camera 250 was mounted onto a second documentation port to enabled simultaneous acquisition of interferometric data and video light microscopy. The OCT axial resolution (Δz in Eq. 1), set by the coherence length of the light source, was measured to be approximately 8.5 um in air. The spectrometer was a low-cost commercial version (Ocean Optics USB-2000) with a spectral acquisition time of 5 ms and a readout time of 20 ms. Repeated spectral measurements were acquired at the same position on the sample as a function of time at the maximum readout rate of the spectrometer. Phase values obtained from a Fast Fourier Transform (FFT) of the re-sampled spectral data at the depth position corresponding to the feature of interest in the sample (i.e., the cell surface) were acquired, and unwrapped in time. Displacements were calculated as per Eq. 4. Timestamps from the video capture and SDPM software were used in post processing to correlate the SDPM and video information collected.

Figure 6A:
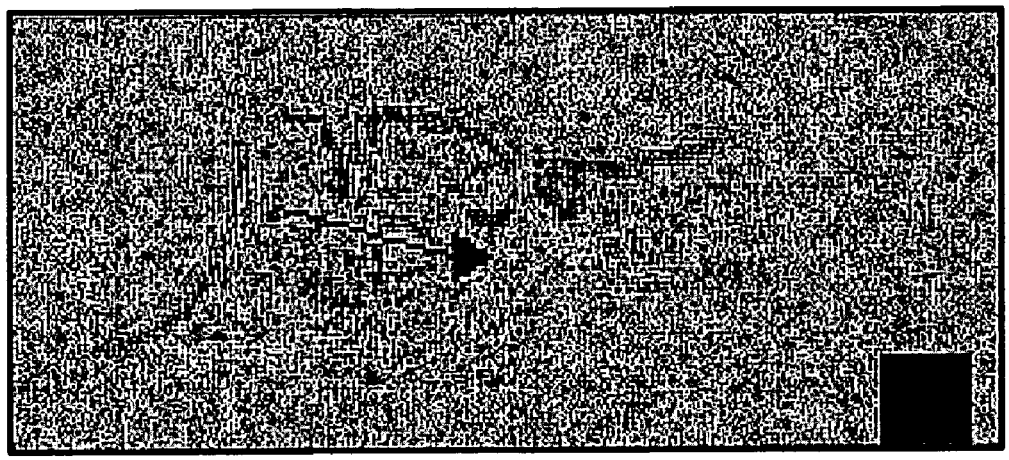
FIG. 6A is a photomicrograph of an isolated ventricular cardiomycocyte from a 2-day old chick embryo.
Figure 6B:
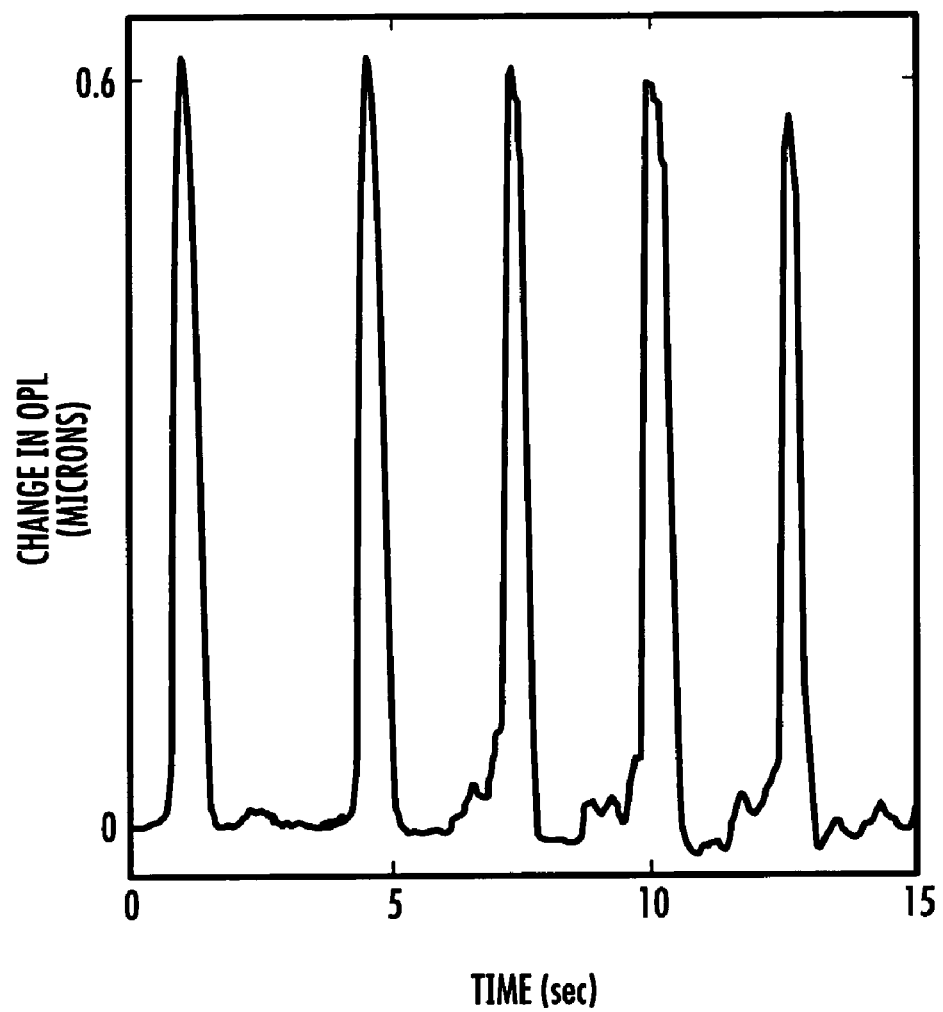
FIG. 6B is a graph of the change in optical path length in microns as a function of time at a position P in FIG. 6A.

Isolated ventricular cardiomyocytes from Day 2 chick embryos were obtained. Cells were plated in dishes with coverglass bottoms that were anti-reflective coated for an air-water interface and maintained at 37° C. (a permissive temperature for spontaneous beating) through contact with a heated stage as shown in FIG. 6A. Individual myocytes were visually located using light microscopy, and the interferometric signals were recorded from a site near the apparent center of contractile motion. Video light microscopy revealed regular cell motions attributed to spontaneous contraction in the examined myocytes. Spectral domain traces (e.g., the phase variations between a plurality of interferometric optical profiles) acquired at the cross-sectional depth corresponding to the cell surface at position P displayed a unique spiked pattern of displacement as shown in FIG. 6B, which appeared synchronously with the beating observed on video microscopy.

Although the magnitude of the spikes was most prominent for phase traces obtained from the cell surface, similar patterns were observed for traces at discrete depths directly adjacent to this, while still within the source coherence length. The magnitude of the optical pathlength change for this single cell was roughly 0.6 µm, which is in good agreement with the magnitude of cell surface motion found in spontaneously contracting myocytes in a previous experiment using near-field scanning optical microscopy.

Sub-Resolution Profiling is Depth-Gated Using Broadband Interferometry

By examining the phase variations between a plurality of interferometric optical profiles to perform structure profiling, broadband (otherwise known as low-coherence) interferometry can be employed both to obtain the interferometric phase information which is the basis of the sub-resolution measurement, as well as to simultaneously gate out all other axially displaced reflections, either from within the sample or from elsewhere in the optical system. The resolution of the coherence gate is given by the coherence length of the light source, and just as in conventional optical coherence tomography, this gate is typically a few micrometers in length and is also a very strong discriminator against reflections from outside of the gate. This coherence gate may be used in many sub-resolution profiling applications, and can serve two functions. First, the coherence gate rejects spurious reflections from optical elements outside of the sample from interfering with the optical phase measurement. Second, the coherence gate enables the selection of a few micrometers of depth in the sample within which surface profiling using the phase variations between a plurality of interferometric optical profiles can be performed.

Depth-Priority Scanning Multidimensional SDPM

As discussed above, nanoscale resolution of depth-gated feature profilometry in samples as a function of temporal delay (by waiting a set delay time between phase acquisitions), or of lateral position (by laterally translating either the sample or the optical beam between phase acquisitions) can be performed. In both cases, the profiling measurement is understood to be obtained in the depth direction (denoted by z in Eqs. 1-5) by processing of spectral interferometric data measured as a function of wavenumber k (possibly requiring re-sampling from wavelength to wavenumber, in the case of SDOCT implementations). Lateral profiling may be extended to scanning in more than one lateral dimension (i.e., both x and y) between phase acquisitions (see FIG. 2), from which data a 2-dimensional surface profile of the structure of interest with nanoscale resolution may be constructed. The lateral scanning may be accomplished using, for example, a raster scan pattern, or any other 2D lateral scan pattern which may be optimized to obtain the data in the order which is optimal for the measurement to be performed. In these implementations, the spectral data may be acquired at each lateral position prior to moving on to the next lateral position, thus this mode of scanning may be referred to as depth-priority scanning. Other scanning approaches may result in a longer time period for acquisition of the spectral data, and small motions of the sample during spectral acquisition may degrade the spectral data thus obtained. If motion of the sample is a concern (as it is likely to be for any living biological sample), the spectral dimension may be acquired rapidly, so that sample motion during spectral acquisition may be less likely to "wash out" the interferometric data. For example, using an SDOCT interferometer set-up (FIG. 2), depth-priority scanning may be accomplished by using a high-speed line camera in the focal plane of a grating-based spectrometer as a high-speed spectrometer. Using the SSOCT interferometer set-up, depth-priority scanning is accomplished by using a rapidly tuned laser source or alternatively, a rapidly tuned tuning element such as a tunable Fabry-Perot cavity placed between a broadband light source and the interferometer.

To conduct multidimensional structural profiling on living samples such as cells for which motion is a concern for inducing fringe washout, serial line- or raster-scanning of the spot from an axial profiling, high-speed optical interferometry system may be used as illustrated in FIG. 2. One- and two-dimensional raster-scanning phase microscopy may be used. The spectral acquisition time of such a system may be limited by the short integration times (down to 30 µs) available from high-speed line-scan cameras utilized in the spectrometer, and the system can remain based on convenient and flexible single mode optical fibers.

Parallel Acquisition Multidimensional Structural Profiling

To accommodate situations where fringe washout is not necessarily a concern, one or more lateral dimensions may be acquired simultaneously using array detectors. These implementations share the characteristic that they are bulk-optic systems where at least one dimension of the sample is directly optically imaged onto one dimension of an array detector (such as a CCD detector or photodiode array), where it overlaps with reference light.

It should be understood that various light sources and detectors can be used to acquire interferometric data according to embodiments of the present invention.

For example, the optical systems 210 and 310 of FIGS. 2 and 3 can be configured as a bulk-optic layout to image one lateral dimension of combined sample and reference light onto one dimension of an array detector, such as a CCD array. In some embodiments, such an interferometric system is illuminated by one wavelength of light from a tunable light source (such as tunable wavelength source 322 of FIG. 3). A one-dimensional lateral image of the sample can be acquired for each wavelength of the tunable light source by the one-dimensional detector. The light source can then be tuned to a second wavelength to acquire a second one-dimensional lateral image. The acquisition of a plurality of such one-dimensional images at a sequence of wavelengths results in a two-dimensional raw dataset including a lateral and a spectral dimension.

As another example, a two-dimensional array detector such as a two-dimensional CCD array or two-dimensional photodiode array can be used to detect light reflected from the sample. The two-dimensional array can be a detector in an imaging spectrometer, such that one lateral dimension of combined sample and reference light is directly imaged onto one of the dimensions of the two-dimensional array detector, while the combined sample and reference light is spectrally dispersed in the orthogonal spatial dimension. Accordingly, every acquisition from the detector array results in a two-dimensional dataset including a lateral and a spectral dimension.

As yet another example, a "full field" optical profile can be obtained using a two-dimensional CCD array and a tunable light source. A common path bulk-optic interferometer can be used to illuminate the sample and detect the back-scattered light on a two-dimensional CCD camera. A two-dimensional lateral image of the sample can be acquired for each wavelength of the tunable light source. The light source can then be tuned to a second wavelength to acquire a second two-dimensional lateral image. The acquisition of a plurality of such two-dimensional images at a sequence of wavelengths results in a three-dimensional raw dataset including two lateral dimensions and a spectral dimension.

Figures 7A, 7B, 7C, 7D, 7E, 7F:
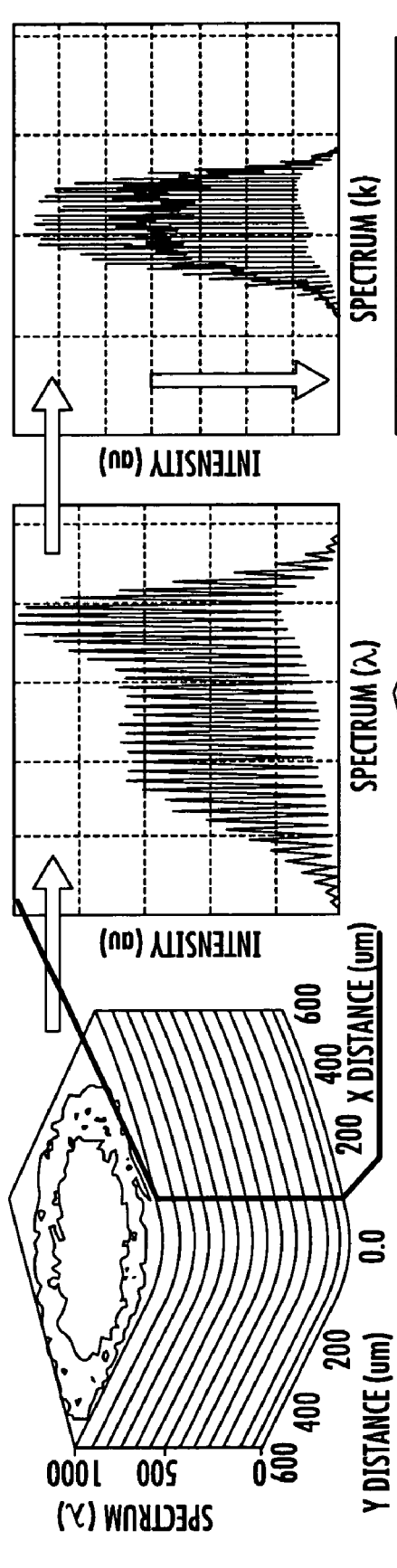
FIGS. 7A-7F are graphs illustrating data processing techniques according to embodiments of the present invention.

Various data processing techniques are illustrated in FIGS. 7A-7F. The raw data acquired by each of the alternate embodiments for each phase measurement comprises a raw spectral interferogram (containing axial data) for each lateral point in a one-dimensional or two-dimensional spatial array (i.e., a spectral dimension by two lateral dimensions). The full three-dimensional dataset may thus be visualized as three-dimensional data cube, with the axial dimension representing spectrum and the other two dimensions representing lateral displacement (FIG. 7A). As discussed above, in some embodiments, only data in only one lateral dimension is acquired. In this case, the data may be considered as a two-dimensional vertical slice through the data cube in FIG. 7A in either the x or y direction. Each of the raw spectral interferograms can be first re-sampled from being unevenly sampled in wavenumber (for example, from being evenly sampled in wavelength as in FIG. 7B) to be evenly sampled in wavenumber, as illustrated in FIG. 7C. Each spectral interferogram is then Fourier transformed into complex reflectivity data having magnitude and phase, as described in Eqs. (2) and (3) and illustrated in FIG. 7D. The phase data is then unwrapped if necessary, and may be converted into distance using Eq. 5. The resulting nanoscale distance profiles as a function of one or two lateral dimensions may be expressed as a horizontal slice through the three-dimensional dataset of FIG. 7E, which has now been transformed into an axial distance as a function of one or two lateral distances. When only data in only one lateral dimension has been acquired, a one-dimensional nanoscale axial distance profile as a function of one lateral direction as shown in each horizontal or vertical slice of FIG. 7E can be calculated. When data in two dimensions has been acquired, a two-dimensional nanoscale axial distance profile as a function of both lateral directions, as illustrated in 7E can be calculated.

Reduction of Artifacts from Phase Corruption

The calculation of pathlength displacement from phase in Eqs. (4) and (5) is generally derived under the assumption that pathlength and phase are generally linearly related. The linearity of this relationship follows directly from Fourier transform analysis, however; this assumption is identically true in the limit that the phase being sampled arises from an isolated reflector. For a band-limited spatial frequency response signal, phase contributions from distant reflectors may be negligible. On the contrary, closely spaced reflectors can degrade the assumed linear relationship between phase and optical pathlength through a process referred to as phase corruption. For example, cells thinner than ~20 μm may suffer from phase corruption when the presence of a strong reflection from the top of the glass coverslip that serves as the reference signal overlaps the reflection from the cell surface, thus adversely influencing the phase values obtained for motion at the cell surface. (Even if the top surface of the cover slips are anti-reflection coated to reduce this effect).

One approach to address this problem is to employ shorter coherence length light sources. However, because femtosecond light sources are very expensive, and because thinner samples will always arise no matter how short the coherence length, an inexpensive algorithmic solution may be used. In addition to resolving sample from reference features, such a solution may also enable imaging of sub-cellular structures that are usually ambiguously incorporated into neighboring structures due to source-constrained limits on axial resolution.

The analysis begins by modifying Eq. (1), the interferometric component of the signal current incident on a single pixel element of a photodiode array used in conventional SDOCT implementations, to allow for a sample with N distinct reflectors. In this case, Fourier transformation yields a complex quantity I(z) whose phase (prior to unwrapping) at spatial domain position z is given by:

$$\theta(z) = \tan^{-1}\left(\frac{\sum_{n=1}^{N} A_n \sin[2k_0(z-z_n)] e^{\frac{-(z-z_n)^2}{2\sigma^2}}}{\sum_{n=1}^{N} A_n \cos[2k_0(z-z_n)] e^{\frac{-(z-z_n)^2}{2\sigma^2}}}\right). \quad (7)$$

Here, n represents each reflector, $A_n$ is the magnitude of the backscattered signal for a reflector at position $z_n$, and the coherence envelope function is written explicitly as a function of the coherence length of the light source σ. The effect of reflector n on the observed phase of reflector n+1 when the two are spaced a distance $z_0$ apart is characterized by the derivative of Eq. 7, which can be written as $$\frac{\partial \theta(z_{n+1})}{\partial t} = k_0 - \frac{yM\sin(k_0 z_0)}{\sigma^2\left(1 + M^2 e^{\frac{z_0^2}{2\sigma^2}} + 2M\cos(k_0 z_0)\right)}, \quad (8)$$

where $M = A_{n+1}/A_n$ is the relative magnitude between the two peaks. In the limit that $z_0 \to \infty$ (the reflectors are very distant) or $M \to \infty$ (the sample is reduced to a single reflector), the slope is identically $k_0$ at all spatial positions z, and the linear relationship between phase and displacement is preserved. Deviation of the slope from this expected value is inevitable when reflectors are too close. As can be seen by Eq. 8, there are four primary contributors to phase corruption: $k_0$ and σ are known parameters of the light source used; while M and $z_0$ are parameters inherent to the sample.

A first approach for correcting for the effects of phase corruption is to estimate values of M and $z_0$ from known properties of the sample, and then to use Eq. (8) to predict a correction factor for the measured displacement data. The separation between the peaks, $z_0$, corresponds to the thickness of the sample, which may be known or be readily estimated. For example, for cell samples $z_0$ may be known a priori (i.e., for standard cell types) or estimated from independent measurements (i.e., from other optical interferometric measurements). For industrial samples, $z_0$ may be known from manufacturing processes or may be measured independently (i.e., from STM or other optical interferometric measurements). The relative magnitude between the peaks, M, may be estimated from the Fresnel reflection magnitudes at the top and bottom boundaries of the sample, given the known indices of refraction of the sample material (i.e., cytoplasm) the structure supporting it (i.e., a glass cover slip), and the air above it.

A second approach for correcting phase corruption due to overlapping reflectors involves acquisition and subtraction of a "background spectrum" which includes all reflectors except the reflector of interest. For the case of a cell or other sample on a cover slip, for example, a suitable background spectrum could be acquired from the cover slip in the absence of the sample. To recover the corrupted phase, the "background" spectrum is subtracted from the raw spectrum data before processing. This subtraction can be done before or after wavelength data are resampled to be evenly spaced in wavenumber. In this approach, the power intensity for all the background reflectors in the two datasets may be matched; however the power intensity can be adjusted by multiplying one or more dataset by a constant factor.

A third approach is as follows. Background spectral data as described above for the second approach can be reconstructed entirely in software, and then used to correct the corrupted dataset as described above. The source spectrum can be recreated and effectively convolved with the point spread function of the spurious reflector that is to be subtracted. For a perfect reflector, this amounts to multiplying the Fourier transform of the source spectrum by a sinusoid whose frequency matches that of the spurious reflector location. To recreate the source spectrum, a low-pass filtered version of the corrupted dataset can be used to extract the raw spectrum, which appears centered at z=0 in the spatial domain because of the DC signal terms. Alternatively, a priori knowledge of the source spectrum can be used to generate a replica of the source. In both methods, knowledge of the point spread function of the reflector may be difficult to ascertain, but in practice the assumption of a perfect reflector may be sufficient.

Noncontact Index of Refraction Measurement

According to embodiments of the present invention, nanoscale optical pathlength measurement capabilities can be used for noncontact index of refraction measurements of a sample. A sample beam of a broadband interferometer can be propagated through the sample, and a plurality of interferometric optical profiles comprising a reference signal propagated through a reference path and the sample signal propagated through the sample can be obtained. Phase variations between the plurality of interferometric optical profiles evaluated at the path length difference between the sample and reference paths can be determined, and variations in an index of refraction of the sample can be identified based on the phase variations. In particular embodiments, the sample includes two media, each having an index of refraction. The index of refraction of the one medium can be calculated based on a known index of refraction of the second medium and the identified variations in the index of refraction of the sample.

For example, a medium within which it is desirable to measure small changes in the index of refraction may be placed in the sample arm of an SDOCT or SSOCT interferometer. A plurality of interferometric optical profiles of a fixed reflector terminating the sample arm may be obtained as a function of depth in an axial direction. Phase variations between the plurality of interferometric optical profiles can be determined, and may be attributed to variations in the index of refraction of the medium traversed by the light in the sample arm. As in previous embodiments, the use of a common-path interferometer design can increase the phase stability of the measurement and thus the accuracy with which index of refraction variations may be measured.

Figure 8A:
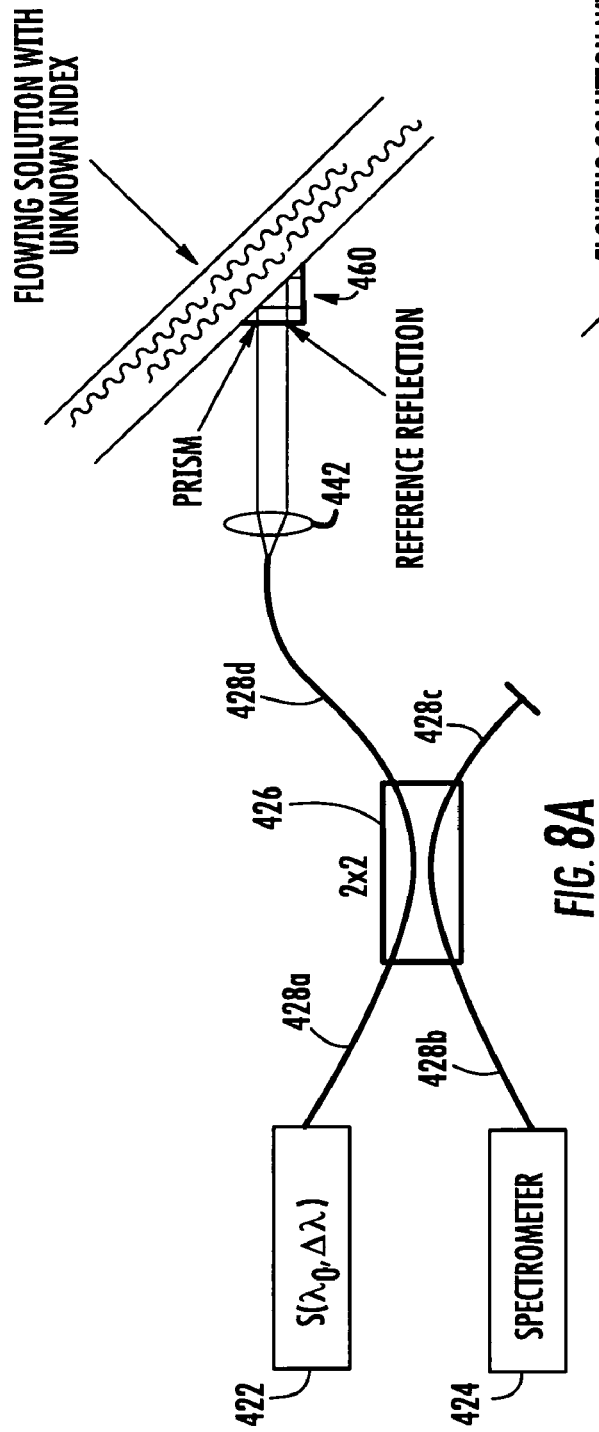
FIG. 8A is a schematic diagraph of an optical system for measuring an index of refraction of a sample.
Figure 8B:
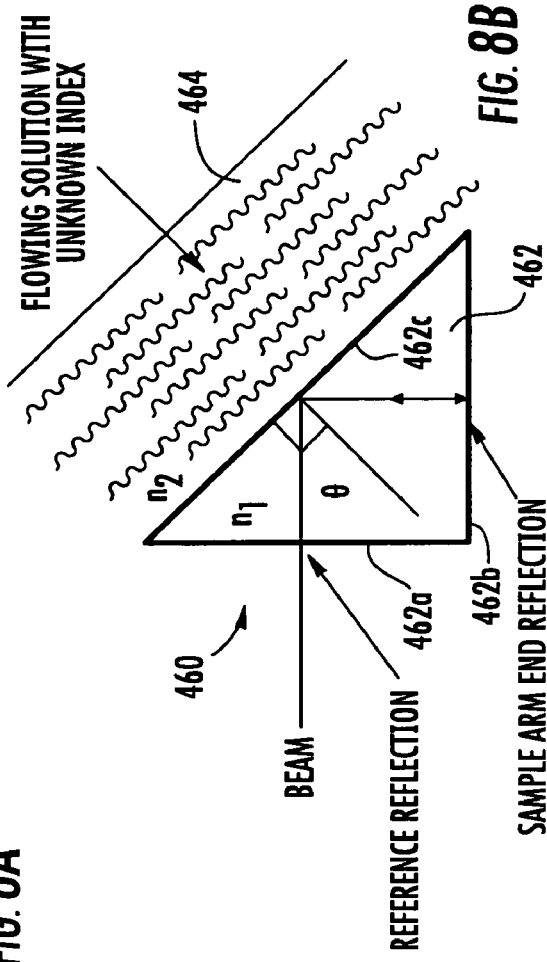
FIG. 8B is an enlarged view of the sample of FIG. 8A.

According to embodiments of the present invention, measurements of small changes in the index of refraction of a medium at an optical interface may be made. In particular, as shown in FIG. 8A, a broadband light source 422 is passed via optical fibers 428a, 428b, 428c and 428d, fiber coupler 426 and lens 442 onto a sample 460. As shown in FIG. 8B, the sample 460 includes a flowing medium 464 and a prism 462. Reflected light is detected by the spectrometer 424. As illustrated, the reference reflection and the sample reflection are both reflected from the sample 460, i.e., a "common path" configuration. The medium 464 can be a solution.

In some applications in biomedical and scientific measurements, it may be desirable to measure changes in the index of refraction of media, such as the flowing medium 464, with high accuracy. For example, a system which is capable of monitoring small changes in the refractive index of a fluid in a flowing tube or a reservoir may have applications in noninvasive sensing of analytes and/or impurities, for example for biochemical analyte sensing in analytical chemistry applications, or for impurity or toxin detection in municipal water systems. Additionally, this type of system may be used in powerful biosensors in which specific molecules or compounds (i.e., antibodies or DNA strands) may be immobilized via chemical means on the dielectric surface, and small changes in refractive index result from attachment of complementary molecules (antigens or complimentary DNA strands) precipitating out of the flowing solution. Such a system based on the noninvasive measurement of refractive index may have the advantage of label-free detection of the analyte, impurity, or molecule of interest, provided that the compound effects the refractive index of the fluid in a known way, and that other confounding effects on the refractive index of the fluid (such as temperature fluctuations or fluctuations in the concentrations of other impurities) can be accounted for.

Accordingly, the techniques described herein can be used for noninvasive monitoring of refractive index. At angles larger than the critical angle for total internal reflection from a planar boundary between dielectric media, the phase of the internal reflection coefficient depends upon the ratio of the refractive indices ($n_1$ and $n_2$ in FIG. 14B) of the media on both sides of the interface. For the TE and TM polarized waves, respectively, $$\tan\left(\frac{\varphi}{2}\right) = \frac{\sqrt{\sin^2\theta - \sin^2\theta_c}}{\cos\theta} \quad (9)$$

and $$\tan\left(\frac{\varphi}{2}\right) = \frac{\sqrt{\sin^2\theta - \sin^2\theta_c}}{\cos\theta \sin^2\theta_c}. \quad (10)$$

In these expressions, $\theta$ is the internal angle of reflection at the interface (illustrated in FIG. 8B), $\theta_c$ is the critical angle for total internal reflection (given by $=\sin^{-1}(n_2/n_1)$), and $\varphi$ is the phase of the reflection coefficient. Accordingly, $\varphi$ corresponds to the phase of the complex reflectivity profile obtained by Fourier transformation of spectral interferogram data according to Eq. (5), evaluated at the axial depth corresponding to the position of a sample reflector wherein the sample arm path includes at least one total internal reflection at the index boundary of interest. As illustrated in FIG. 8B, the flowing medium 464 is in contact with the hypotenuse of a glass prism of known refractive index $n_1$, for example a right angle prism 462. The common-path reference and sample light is incident on the prism 462 normal to one of the faces 462a thereof, and the reflection from the face 462a is used as the reference reflection for spectral interferometry (this reflection may be coated to provide a reference reflectivity which optimizes the signal-to-noise ration of the interferometric measurement). The sample arm light which traverses the face 462a is substantially internally reflected at the hypotenuse of the prism 462, and is incident at normal incidence to the other flat face 462b. Light retro-reflected from the face 462b (which may optionally be coated to be more efficiently reflected) is used as the sample arm end reflection, and the sample arm light thus re-traces its path through a second total internal reflection at the hypotenuse face 462c of the prism 462, and re-joins the reference light at the incident path. So long as the angle of incidence $\theta$ at the hypotenuse reflection is greater than the critical angle $\theta_c$, the interface satisfies the condition for total internal reflection and the phase of the reflection at that interface will be described by Eqs. (9) and (10) for the respective polarization states. Thus, small changes in the refractive index of the fluid outside of the hypotenuse face 462c of the prism, $n_2$, can result in measureable changes in the phase of the complex reflectivity profile from Eq. (3), evaluated at the depth position corresponding to the sample reflection from the face 462b of the prism.

As illustrated in FIGS. 8A-8B, which use a right angle prism, the angle with which the sample reflection is incident on the hypotenuse face 462C of the prism is 45 degrees, thus the critical angle $\theta_c$ is less than 45 degrees. The angle $\theta_c$ for an interface between standard borosilicate glass ($n_1=1.5$) and air ($n_2=1.0$) satisfies this condition ($\theta_c=41$ degrees); thus this system may be used to monitor small changes in the index of refraction of air or other gases due to impurities or other factors. If the fluid has an index of refraction close to that of water ($n_2=1.33$), then a right-angle prism with a higher index of refraction ($n_1>1.88$) must be used to ensure that $\theta>\theta_c$.

Although FIGS. 8A-8B are illustrated with respect to a flowing medium 464 and a prism 462, it should be understood that other configurations can be used to measure an index of refraction. For example, optical setups may be designed to allow for reference and sample reflections to be obtained for smaller angles of incidence on the index interface of interest (i.e., by not using a right-angle prism or by not using the front and back faces of a right-angle prism for the reference and sample reflections). For example, a transmissive sample arm could be designed which executes only a single reflection from the index of refraction boundary, and re-joins the reference light using an optical circulator or coupler. In addition, alternative optical setups may also be readily designed to more closely match the reference and sample optical paths, in case the pathlength through the prism is too great given the spectral resolution of the SDOCT or SSOCT system used to collect and process the spectral interferometric data. In some embodiments, the phase of an internal reflection may thus be monitored from a refractive interface (either in single or double pass), and small changes in the refractive index of the material on the other side of the interface may be monitored noninvasively.

In some embodiments, the phase difference upon total internal reflection at a boundary may be substantially increased beyond that indicated in Eqs. (9) and (10) by using the principles and techniques of surface plasmon resonance (SPR). Common-path phase-shift interferometry techniques have been used in biosensing systems for measuring phase variations caused by biomolecular interactions on SPR sensing chips without the need for additional labeling. A phase variation which is several orders of magnitude more sensitive to external refractive index variations that indicated in Eqs. (9) and (10) may be achieved by coating the refractive interface boundary with a thin film of gold metal, and adjusting the angle of reflection to the well-characterized SPR angle. Then, the measurements of phase differences described herein can be performed.

In the drawings and specification, there have been disclosed typical preferred embodiments of the invention and, although specific terms are employed, they are used in a generic and descriptive sense only and not for purposes of limitation, the scope of the invention being set forth in the following claims. Moreover, various spectrometer and detector configurations and techniques known to those of skill in the art may be used to accomplish the functions and features of the embodiments described herein.

What is claimed is:

1. A method of identifying structure profiles from optical interferometric data comprising:
    obtaining a plurality of broadband interferometric complex optical profiles of a structure as a function of structure depth in an axial direction, each of the plurality of interferometric complex optical profiles comprising a reference signal propagated through a reference path and a sample signal reflected from a sample reflector, wherein the interferometric complex optical profile include magnitude data and phase data as a function of depth;
    selecting at least one axial region corresponding to at least a portion of the structure;
    determining phase variations between the phase data of the plurality of interferometric complex optical profiles at the selected axial position; and
    identifying a physical profile of the structure based on the phase variations of the phase data at the selected axial position.

2. The method of claim 1, wherein the broadband interferometric complex optical profiles are obtained using a light source spectrum of at least about 10 nanometers.

3. The method of claim 1, wherein the plurality of interferometric complex optical profiles are acquired at the selected axial position as a function of time.

4. The method of claim 1, wherein the plurality of complex optical interferometric profiles are acquired at the selected axial position as a function of one or more lateral positions.

5. The method of claim 1, wherein the plurality of complex optical interferometric profiles are a complex reflectivity profile obtained from a Fourier or inverse Fourier transform of a broadband spectral interferogram.

6. The method of claim 1, wherein a resolution of the physical profile of the structure is less than about 10 nanometers.

7. The method of claim 1, wherein the structure comprises a portion of a biological cell.

8. The method of claim 7, wherein the portion of the biological cell includes a cell surface.

9. The method of claim 1, wherein the plurality of complex optical interferometric profiles are acquired using an interferometer having a substantially common sample and reference pathway.

10. The method of claim 1, wherein the plurality of complex optical interferometric profiles are acquired using a Spectral Domain Optical Coherence Tomography (SDOCT) interferometer.

11. The method of claim 1, wherein the plurality of complex optical interferometric profiles are acquired using a Swept Source Optical Coherence Tomography (SSOCT) interferometer.

12. The method of claim 1, further comprising estimating the extent of phase nonlinearity at the selected axial position due to the presence of multiple closely spaced reflectors, and calculating a reduction of the nonlinearity for the resulting structure profile.

13. A system for identifying structure profiles from optical interferometric data comprising:
    an interferometer configured to acquire a plurality of broadband interferometric complex optical profiles of a structure as a function of structure depth in an axial direction, each of the plurality of interferometric complex optical profiles comprising a reference signal propagated through a reference path and a sample signal reflected from a sample reflector in the axial direction, wherein the complex optical profiles include magnitude data and phase data as a function of depth; and
    a signal analyzer configured to select at least one axial position corresponding to at least a portion of the structure, to determine phase variations between the phase data of the plurality of interferometric complex optical profiles at the selected axial position, and to identify a physical profile of the structure based on the phase variations of the phase data at the selected axial position.

14. The system of claim 13, wherein the interferometer includes light source having an instantaneous or tunable spectrum of at least about 10 nanometers.

15. The system of claim 13, further comprising a controller configured to control the interferometer to acquire the plurality of complex optical interferometric profiles at the selected axial position as a function of time.

16. The system of claim 13, further comprising a controller configured to control the interferometer to acquire the plurality of complex optical interferometric profiles at the selected axial position as a function of one or more lateral positions.

17. The system of claim 13, wherein the plurality of complex optical interferometric profiles are a Fourier transform complex reflectivity profile of a broadband spectral interferogram.

18. The system of claim 13, wherein a resolution of the physical profile of the structure is less than about 10 nanometers.

19. The system of claim 13, wherein the structure comprises a portion of a biological cell.

20. The system of claim 19, wherein the portion of the biological cell includes a cell surface.

21. The system of claim 13, wherein the interferometer has a substantially common sample and reference pathway.

22. The system of claim 13, wherein the interferometer is a Spectral Domain Optical Coherence Tomography (SDOCT) interferometer.

23. The system of claim 13, wherein the interferometer is a Swept Source Optical Coherence Tomography (SSOCT) interferometer.

24. A computer program product for identifying structure profiles of optical interferometric data comprising:
   a computer readable medium having computer readable program code embodied therein, the computer readable program code comprising:
   computer readable program code configured to obtain a plurality of broadband interferometric complex optical profiles of a structure as a function of structure depth in an axial direction, each of the plurality of interferometric complex optical profiles comprising a reference signal propagated through a reference path and a sample signal reflected from a sample reflector in the axial direction, wherein the complex optical profiles include magnitude data and phase data as a function of depth;
   computer readable program code configured to select at least one axial position corresponding to at least a portion of the structure;
   computer readable program code configured to determine phase variations between phase data of the plurality of interferometric complex optical profiles at the selected axial position; and
   computer readable program code configured to identify a physical displacement of the structure based on the phase variations of the phase data at the selected axial position.

25. The method of claim 1, wherein the physical profile of the structure includes sub-coherence length resolution.

26. The system of claim 13, wherein the physical profile of the structure includes sub-coherence length resolution.

27. The computer program product of claim 24, wherein the physical profile of the structure includes sub-coherence length resolution.

* * * * *

UNITED STATES PATENT AND TRADEMARK OFFICE
CERTIFICATE OF CORRECTION

| | |
|---|---|
| PATENT NO. | : 7,633,627 B2 |
| APPLICATION NO. | : 11/337166 |
| DATED | : December 15, 2009 |
| INVENTOR(S) | : Choma et al. |

It is certified that error appears in the above-identified patent and that said Letters Patent is hereby corrected as shown below:

Column 10, Line 30: correct "$\delta z(t)=$" in formula (5) to read -- $\delta z(x)=$ --.

Signed and Sealed this

Eighth Day of June, 2010

David J. Kappos
*Director of the United States Patent and Trademark Office*

UNITED STATES PATENT AND TRADEMARK OFFICE
CERTIFICATE OF CORRECTION

PATENT NO.       : 7,633,627 B2
APPLICATION NO. : 11/337166
DATED            : December 15, 2009
INVENTOR(S)      : Choma et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 340 days.

Signed and Sealed this

Ninth Day of November, 2010

David J. Kappos
*Director of the United States Patent and Trademark Office*